(12) United States Patent
Miska et al.

(10) Patent No.: US 8,378,667 B2
(45) Date of Patent: Feb. 19, 2013

(54) SYSTEM AND METHOD FOR DETECTING THE PASSAGE OF AN OBJECT IN PIPELINE INCLUDING SHIELDED MAGNETOMETER AND A MICROCONTROLLER WITH ADAPTIVE THRESHOLDING DETECTION MEANS

(75) Inventors: Stephen J. Miska, Tulsa, OK (US); William J. Rankin, Sapulpa, OK (US); Matthew W. Logan, Broken Arrow, OK (US); Mark G. Register, Broken Arrow, OK (US); Eric N. Freeman, Kiefer, OK (US); Philip M. Maltby, Tulsa, OK (US); Lloyd N. Salsman, Stillwater, OK (US)

(73) Assignee: TDW Delaware Inc., Wilmington, DE (US)

( * ) Notice: Subject to any disclaimer, the term of this patent is extended or adjusted under 35 U.S.C. 154(b) by 555 days.

(21) Appl. No.: 12/470,654

(22) Filed: May 22, 2009

(65) Prior Publication Data

US 2010/0295543 A1    Nov. 25, 2010

(51) Int. Cl.
*G01B 7/14* (2006.01)
*G01N 27/72* (2006.01)
(52) U.S. Cl. .................. 324/207.26; 324/220; 324/221; 324/207.24; 324/207.22
(58) Field of Classification Search .......... 324/220–221, 324/207.11–207.26
See application file for complete search history.

(56) References Cited

U.S. PATENT DOCUMENTS

| | | | |
|---|---|---|---|
| 3,443,211 A * | 5/1969 | Walters et al. ................ | 324/232 |
| 3,673,629 A | 7/1972 | Casey et al. | |
| 3,878,453 A | 4/1975 | Potter et al. | |
| 3,888,260 A | 6/1975 | Fischell | |
| 3,975,772 A * | 8/1976 | Lin .............................. | 360/317 |
| 4,091,322 A | 5/1978 | Stankoff | |

(Continued)

FOREIGN PATENT DOCUMENTS

| EP | 1397541 | 6/1975 |
|---|---|---|
| WO | WO 99/32902 | 7/1999 |

(Continued)

OTHER PUBLICATIONS

International Search Report and Written Opinion issued by the International Searching Authority (ISA/US) on Jun. 1, 2010 in PCT/US2010/029967 (10 pgs).

(Continued)

*Primary Examiner* — Jay Patidar
(74) *Attorney, Agent, or Firm* — Gable Gotwals (57) ABSTRACT

A pipeline pig signal made according to this invention houses one or more shielded magnetometer sensors and a microcontroller with adaptive thresholding detection means for reducing the likelihood of false alarms. The adaptive thresholding detection means removes outlier data from the magnetic flux data stream and then passes the outlier-free data stream through four low pass filters. A smoothed magnitude of the data stream is compared to detection limits and, if a passage event has occurred, a recent detection is indicated, a counter of a display unit is incremented, a time of passage is recorded, and both statistics are displayed on the display unit. Because a single object may produce multiple magnetic fields, the detector may be locked-out for a predetermined period of time after the passage event to prevent a second detection of the same object as it passes the detection device.

32 Claims, 11 Drawing Sheets

U.S. PATENT DOCUMENTS

| | | | |
|---|---|---|---|
| 4,134,061 A | 1/1979 | Gudgel | |
| 4,427,943 A | 1/1984 | Cloutier et al. | |
| 4,430,613 A | 2/1984 | French | |
| 4,439,730 A | 3/1984 | Kauffman | |
| 4,491,018 A | 1/1985 | Stringer et al. | |
| 4,714,888 A | 12/1987 | French et al. | |
| 4,857,851 A | 8/1989 | Anderson et al. | |
| 5,030,911 A * | 7/1991 | Lam | 324/226 |
| 5,065,098 A | 11/1991 | Salsman et al. | |
| 5,122,744 A | 6/1992 | Koch | |
| 5,126,654 A | 6/1992 | Murphy et al. | |
| 5,417,112 A | 5/1995 | Rosenberg | |
| 5,461,312 A * | 10/1995 | Hosohara et al. | 324/220 |
| 5,506,505 A | 4/1996 | Worthen et al. | |
| 5,651,638 A | 7/1997 | Heggerud | |
| 5,963,042 A | 10/1999 | Suyama et al. | |
| 6,087,830 A | 7/2000 | Brandly et al. | |
| 6,097,189 A | 8/2000 | Arndt et al. | |
| 6,243,657 B1 | 6/2001 | Tuck et al. | |
| 6,339,328 B1 | 1/2002 | Keene et al. | |
| 6,404,189 B2 | 6/2002 | Kwun et al. | |
| 6,489,771 B1 | 12/2002 | Farque | |
| 6,965,320 B1 | 11/2005 | Casey et al. | |
| 7,402,999 B2 | 7/2008 | Plotnikov et al. | |
| 2003/0055321 A1 | 3/2003 | Watrous et al. | |
| 2003/0117134 A1 * | 6/2003 | Almaguer | 324/221 |
| 2004/0227509 A1 * | 11/2004 | Ucan | 324/220 |
| 2006/0076951 A1 | 4/2006 | Nestleroth et al. | |

FOREIGN PATENT DOCUMENTS

| | | |
|---|---|---|
| WO | WO 2008/046209 | 4/2008 |

OTHER PUBLICATIONS

Karki. Active Low-Pass Filter Design, Appln Report SLOA049A—Oct. 2000. http://www.science.unitn.it~bassi/Signal/Tlnotes/sloa049.pdf> (24 pgs).

* cited by examiner

SYSTEM AND METHOD FOR DETECTING THE PASSAGE OF AN OBJECT IN PIPELINE INCLUDING SHIELDED MAGNETOMETER AND A MICROCONTROLLER WITH ADAPTIVE THRESHOLDING DETECTION MEANS

BACKGROUND OF THE INVENTION

This invention relates generally to pipeline monitoring systems and more particularly concerns a sensor for detecting passage of an object, such as a pipeline pig, through a pipeline.

Various means have been developed for detecting the passage of a pig through a pipeline. "Dumb pigs" or "smart pigs" may be detected by intrusive mechanical devices such as threaded adapters with spring-loaded shafts. The shaft has an exposed end with a spring loaded-lever or flag and an opposing end that extends into the interior space of the pipe. Intrusive detection devices, however, require making a hole or hot-tapping into an active piping, an often costly and inconvenient process for a pipeline operator. As a result, non-intrusive detection devices, which are fully located outside of the pipeline and do not require additional hot-tapping or welding, are often preferred by the pipeline operator.

There are two main types of non-intrusive detection devices: acoustic/ultrasonic detectors, which detect a change in sound, and electromagnetic detectors, which detect a change in ambient magnetic field. Passive acoustic detectors can detect a change in sound caused by an object travelling through a pipeline but cannot easily distinguish between this sound change and that caused by a surrounding noise such as a pump or motor vehicle. Active acoustic detectors can eliminate this problem by transmitting an ultrasonic signal, but these devices are costly, require a high level of power and, because of the power requirements, limit or prevent battery-power options.

Electromagnetic detectors often use one or more coils to detect a change in magnetic flux over time. A change in the ambient magnetic field inducts a voltage in the coil or coils proportional to the change of the magnetic field over time. As a result, a slow travelling ferromagnetic object may not generate enough voltage in the coils to generate a detection event.

Magnetometers—which determine a change in magnetic flux by measuring the instantaneous flux over time—are not object-speed dependent. Magnetometers, therefore, can detect any object causing a change in the electromagnetic field regardless of object speed. Magnetometers, however, can be subject to false alarms. Therefore, appropriate methods must be used for noise cancellation, signal processing, and shielding of ambient magnetic fields.

SUMMARY OF THE INVENTION

A system and method for detecting the passage of an object in a pipeline includes a non-intrusive detection device that houses one or more shielded magnetometer sensors and a microcontroller with adaptive thresholding detection means. An AC/DC power source with a backup battery source is employed to provide power to the device. The battery backup power source is preferably configured to break electrical contact prior to exposure to ambient environment, thereby making the detection device suitable for use in explosion-proof zones.

The magnetometer sensors are preferably magnetic flux sensors using a variable permeability material to directly measure flux and are arranged orthogonal to one another. The inner shield surrounding the sensors is an electrically insulating material. The outer shield is a magnetic permeable material. A display unit in communication with the microcontroller displays various statistics, including the number of objects detected and the time of their passage.

The detection device may have an adjustable end for orienting the display unit and positioning the magnetometer sensors near the exterior surface of the pipeline. A reed switch or other means for locking out the detection device may be used when positioning the device on the pipeline or when moving it to a different location on the pipeline. Once the detection device is in its proper position and unlocked, the magnetometer sensors and microcontroller, which process the input magnetic flux data stream, can signal a detection.

The adaptive thresholding detection means employed first removes the outlier data from the magnetic flux data stream. This outlier-free data stream is then passed through four low pass filters. The first low pass filter estimates a baseline by removing a bias value from the magnetic flux data stream and limiting the data stream to a value no greater than an outlier limit. The second low pass filter then uses the baseline estimate to produce a noise estimate. The third low pass filter is a boxcar filter that provides a smoothed magnitude of the data stream. The smoothed magnitude is compared to a set of upper and lower detection limits and then passed through the fourth low pass filter to determine the length of a passage event. If a passage event has occurred, a counter of the display unit is incremented and a time of passage is recorded. Because a single object may produce multiple detections or detection events, the detector may be locked-out for a predetermined period of time after the passage event to prevent a second detection of the same object as it passes the detector. A Bayesian lockout estimator is preferred for this purpose.

A better understanding of the invention will be obtained from the following detailed description of the preferred embodiments taken in conjunction with the drawings and the attached claims.

BRIEF DESCRIPTION OF THE DRAWINGS

FIG. 1 is a front view of an embodiment of a non-intrusive detector made according to this invention. A sensor board (see FIGS. 8 to 11B) that includes a microcontroller and at least one magnetometer sensor ("sensor") is located in a lower portion of the sensor housing. The sensor housing threads into a base structure, which is detachably secured to the pipe, until the bottom of the housing contacts the pipe surface. A display housing, located at the upper end of a conduit assembly section, houses a digital display that indicates the detection of an object within the pipeline as it passes under the detector. A field wiring conduit box is provided for connecting the detector to an AC/DC power source and for accommodating wiring to communicate with, for example, a control room that is controlling the opening and closing of pipeline valves.

FIG. 2 is a side view of the embodiment illustrated in FIG. 1. The display housing houses an assembly that includes a digital display insert and a DC power source (see FIGS. 6 & 7). As the threaded cap at the rear of the display housing is being unthreaded, the DC power source is disconnected, thereby providing a safe environment for use of the detector in explosion-proof zones.

FIG. 3 is a front view of the display panel of FIG. 1. A magnetic reed switch located on the front of the panel resets a timer on the display. A second magnetic reed switch places the detector in locked or unlocked mode and allows an operator to scroll through an object detection history. When in locked mode, the device is prevented from detecting objects and the detector may be moved between locations on the pipeline without resulting in an undesired detection. A battery icon displays battery life if the detector is battery-powered.

FIG. 9 is a view of the shielding for the sensor board of FIG. 8. The inner shield is preferably an electrically insulating material. The outer shield is preferably a magnetic permeable material.

FIG. 10 is a view of the sensor board of FIG. 8. The sensor board includes an interface for communication with the display (which could be a remote located display) or a control system, a microcontroller that runs an adaptive thresholding algorithm (see FIGS. 12 to 19), and a sensor. The sensor is preferably a magnetic flux sensor using a variable permeability material to directly measure magnetic flux.

DETAILED DESCRIPTION OF THE PREFERRED EMBODIMENTS

The magnetometer-based detector that is described below is not limited in its application to the details of the construction, arrangement of the parts, and process flows illustrated in the accompanying drawings. The invention is capable of other embodiments and of being practiced or carried out in a variety of ways. The phraseology and terminology employed herein are for purposes of description and not limitation.

Elements shown by the drawings are identified by the following numbers:

| | |
|---|---|
| 10 | Detector |
| 20 | Sensor housing/module |
| 21 | Upper end of 20 |
| 23 | Lower end of 20 |
| 25 | Threaded portion of 20 |
| 30 | Conduit assembly section |
| 31 | Fill plug |
| 33 | Field wiring conduit box |
| 35 | Tee fitting |
| 37 | Upper end of 30 |
| 40 | Mounting base |
| 41 | Brackets |
| 43 | Shackle pin |
| 45 | Turnbuckle |
| 47 | Chain |
| 50 | Sensor board |
| 51 | Micro-controller |
| 53 | Oscillator |
| 55 | Communication interface |
| 60 | Magnetometer sensor |
| 61 | Inner insulating shield |
| 63 | Outer shield |
| 70 | Display insert/module |
| 71 | Digital display |
| 72 | Insert body |
| 73 | Object count cumulative indicator |
| 74 | Slot in 72 |
| 75 | Object count history indicator |
| 77 | Object icon |
| 79 | Time since last reset indicator |
| 81 | Time since object passage in history indicator |
| 83 | Power status indicator |
| 85 | Locked/unlocked status indicator |
| 87 | Light emitting diode |
| 89 | Reed switch |
| 90 | Display housing |
| 91 | Front cap |
| 93 | Rear cap |
| 94 | Battery pack |
| 95 | Cradle/battery holder |
| 97 | Batteries |
| 99 | Insulating pad |
| 100 | Detection algorithm |
| 110 | Outlier removal algorithm |
| 130 | Baseline estimate algorithm |
| 150 | Noise estimate algorithm |
| 170 | Input smoothing algorithm |
| 190 | Detection event algorithm |
| 210 | Time discriminator algorithm |
| 230 | Lockout discriminator algorithm |

Figure 1:
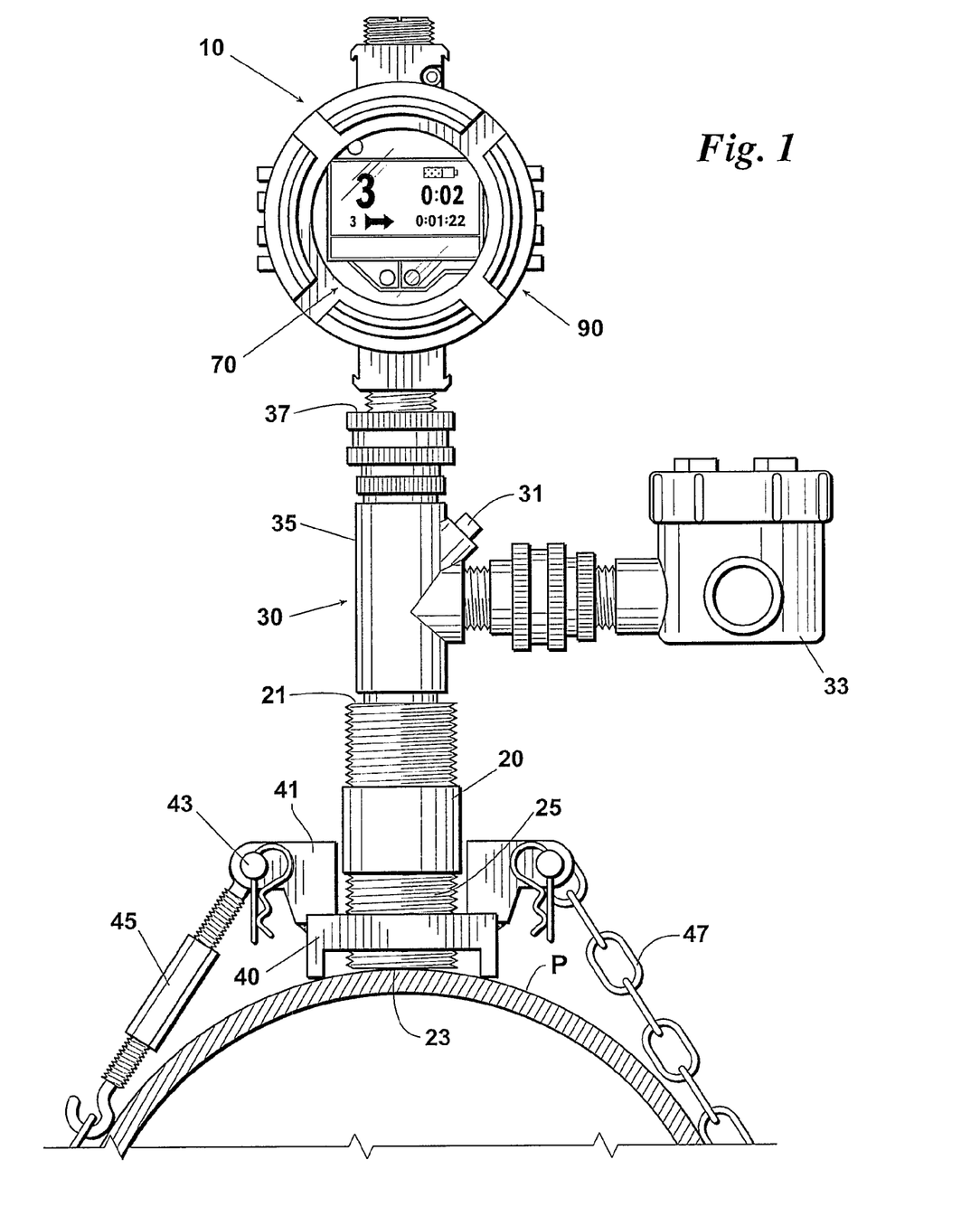
Figure 10:
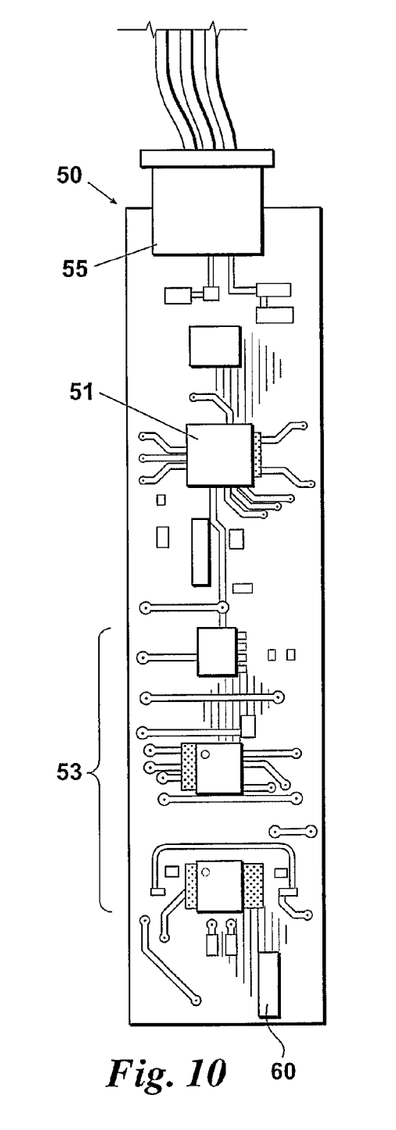
Figures 12, 13:
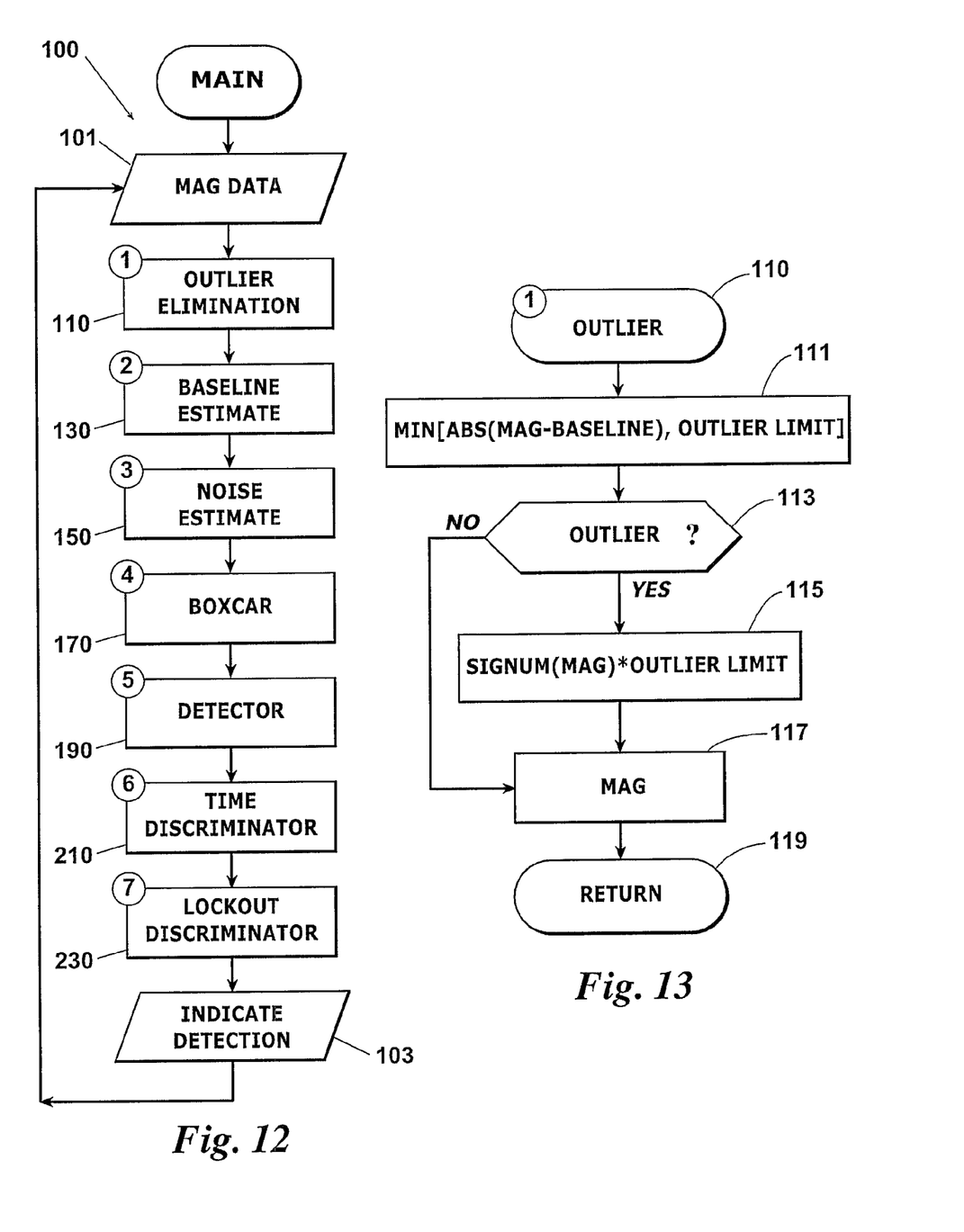
FIG. 12 is a flowchart of a signal processing algorithm implemented by the microcontroller for processing data collected by an n-D array of sensors. The detection scheme is an adaptive thresholding algorithm utilizing a real-time noise estimate for the sensor or sensors.
FIG. 13 is a flowchart of the outlier removal step of the algorithm illustrated in FIG. 12.

Referring first to FIGS. 1, 10 & 12, a detector 10 that is located external to a pipeline section P employs a magnetometer sensor 60 and a detection algorithm 100 to detect the presence of an object in the pipeline. The object may be in motion inside the pipeline section P with detector 10 stationary on the pipeline. The object in the pipeline may be a "pig" used for pipeline maintenance or inspection. The object may carry a magnetic source or intrinsic properties of the object may allow detection. An example of an intrinsically marked object would be a "brush" pig or a pig containing a sizable amount of ferromagnetic material.

Measurements from the magnetometer sensor 60 are processed by detection algorithm 100, which is an adaptive thresholding algorithm, to produce a "passage event." This event may be displayed and/or counted by a digital display 70 or light emitting diode 87. The event can also trigger outputs used to signal remote devices such as a control system for controlling the opening and closing of valves in the pipeline.

Figure 2:
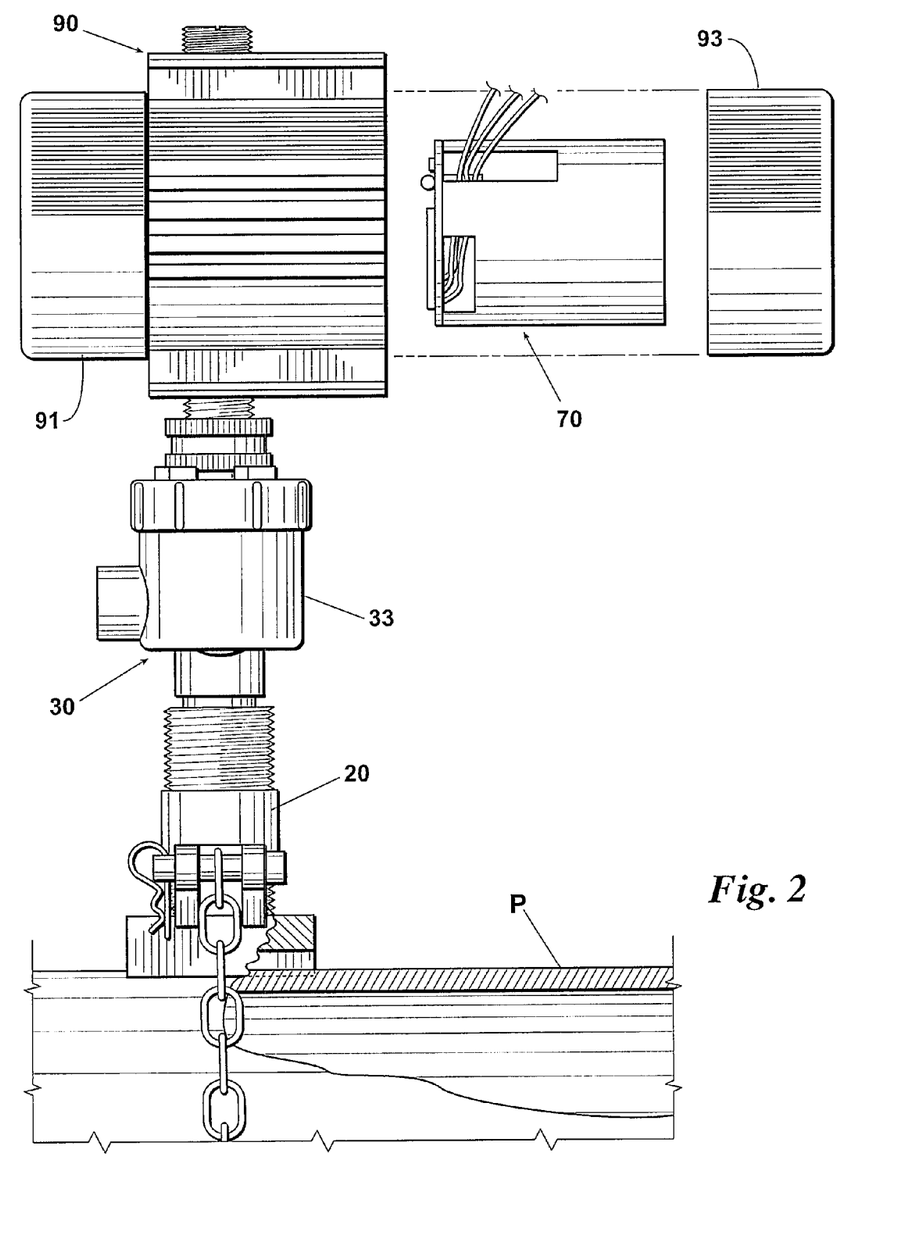

As illustrated in FIGS. 1 & 2, detector 10 is detachably secured to pipeline section P by way of a mounting base 40 that receives a threaded portion 25 of sensor housing 20. This arrangement provides the capability to (1) adjust the distance between the lower end 23 of sensor housing 20 and the external wall surface of pipeline section P and (2) orient the direction of display housing 90. Threaded portion 25 is preferably threaded into base 40 until the lower end 23 of threaded portion 25 makes contact with the external wall surface of pipeline section P. Two opposing brackets 41 of base 40 each receive a shackle pin 43 and an end of chain 47. Chain 47, along with turnbuckle 45, is used to secure base 40 in a desired location on pipeline section P. The above adjustability feature of detector 10 provides the ability to position magnetometer sensor 60 for maximum detection capability.

Located at the upper end 37 of conduit assembly section 30 is a display housing 90. Display housing 90 is preferably detachably secured to conduit assembly section 30. Display housing 90 receives a display insert 70 that provides various indicators and statistics (see text below discussing FIGS. 3 to 5). Symmetrical slots 74 located on the periphery of the insert body 72 ensure the correct orientation of the display 71 and provide necessary wiring access. A front cap 91 of display housing 90 provides a window for the digital display 71 of display insert 70.

Conduit assembly section 30 is located at the upper end 21 of sensor housing 20. The conduit assembly section 30 includes a tee fitting 35 for connecting detector 10 to a field wiring conduit box 33. Conduit box 33 may include wiring for placing detector 10 in communication with an AC/DC power supply, for hardwiring detector 10 to a control room, or for providing wiring to a remote display insert 70. A fill plug 31 may also be provided to add packing, filler, potting compound or sealant.

Figure 3:
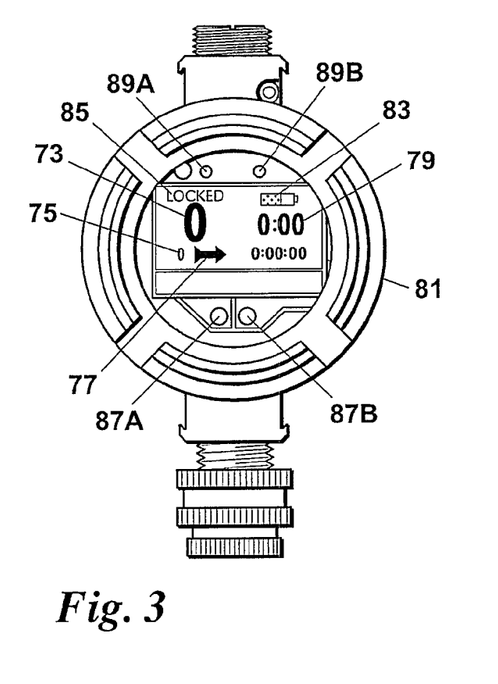
Figure 4:
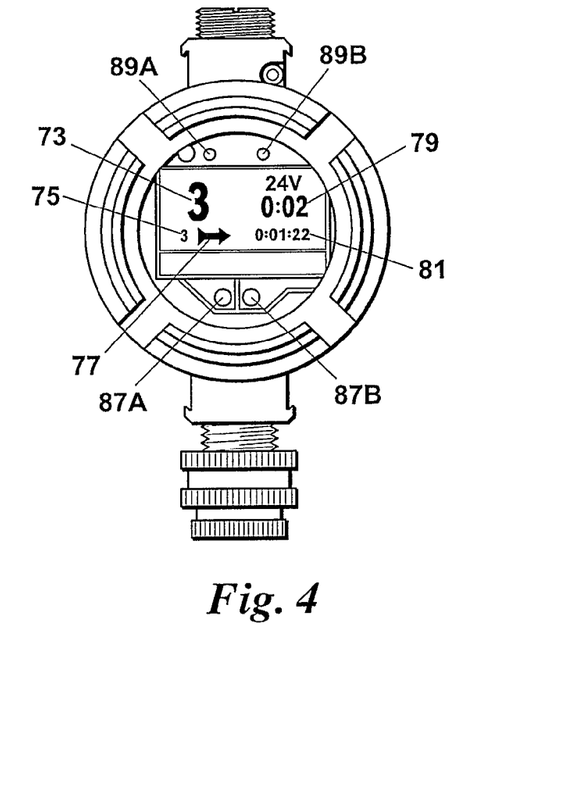
FIG. 4 is another front view of the display panel of FIG. 1 indicating that the detector is hard wired to an AC/DC power source (e.g., 24V power source) and the batteries are not in use. Visual indicators are provided to display statistics such as the number of objects that have been detected, time since detection of any object in the history, and time elapsed since reset.
Figure 5:
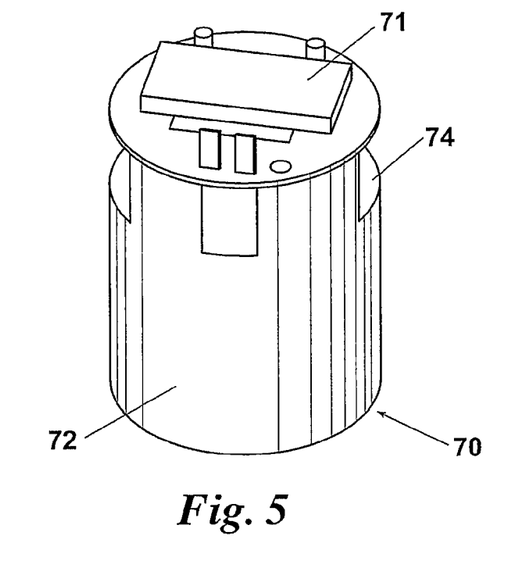
FIG. 5 is an isometric view of the display insert illustrated in FIG. 2. The display panel and digital display is located at the upper end of the assembly. Symmetrical slots are provided about the periphery of the insert body to retain the insert in the display housing and to ensure correct orientation of the display and provide adequate internal wiring access.
Figure 8:
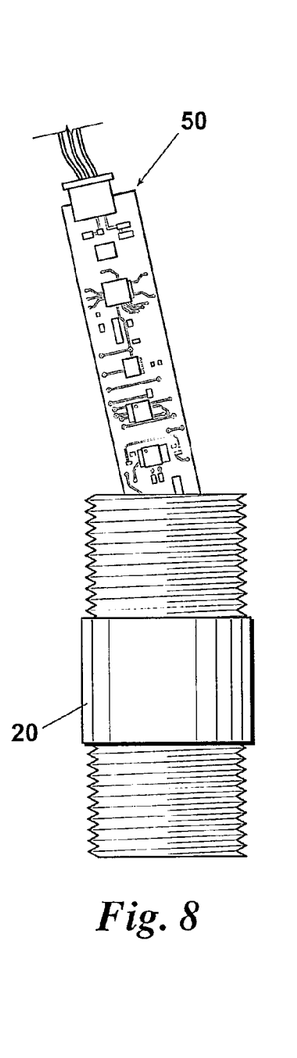
FIG. 8 is a view of the sensor housing. The sensor housing receives the sensor board that includes the microcontroller and the magnetometer sensor.
Figure 9:
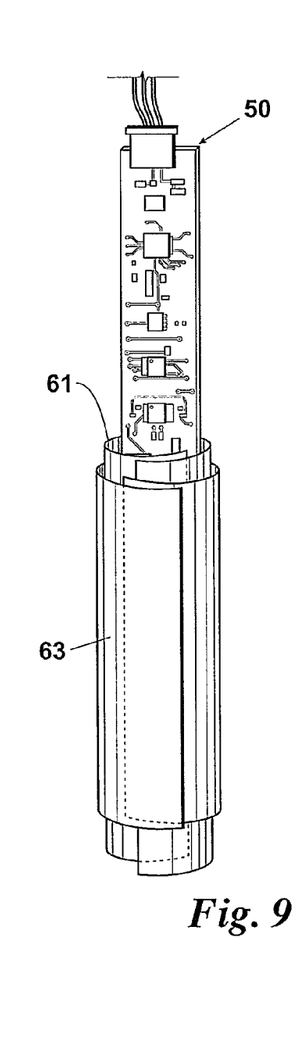

Referring now to FIGS. 3 to 5, display insert 70 may include a digital display 71 that displays various indicators and statistics. In a preferred embodiment, digital display 71 displays an object count indicator 73, an object passage history indicator 75, an object icon 77, a time since last reset indicator 79, and a time since last object in history indicator 81. A microcontroller (not shown) on display 71 receives information from the microcontroller 51 and magnetometer sensor 60 located on sensor board 50 (see FIG. 8).

Display insert 70 also includes a power source indicator 83 that indicates whether detector 10 is operating under battery power (FIG. 3) or AC/DC power (FIG. 4). When on battery power, power source indicator 83 preferably displays a battery icon 83 that indicates battery life.

Digital display 71 also includes a locked/unlocked status indicator 85. A magnetic reed switch 89B places detector 10 in the locked or unlocked mode, thereby providing the ability to control unwanted detection. When in locked mode, detector 10 is prevented from detecting objects and may be moved between locations on the pipeline. Reed switch 89B also allows a user to interact with the statistics and scroll through the object history as indicated by indicators 75 and 81. A second magnetic reed switch 89A resets timer 79. Display unit 70 also includes light-emitting diode indicators 87 to indicate whether a recent passage occurred. Light-emitting diode indicators 87A and 87B light up when reed switches 89A and 89B are triggered, respectively.

Figure 6:
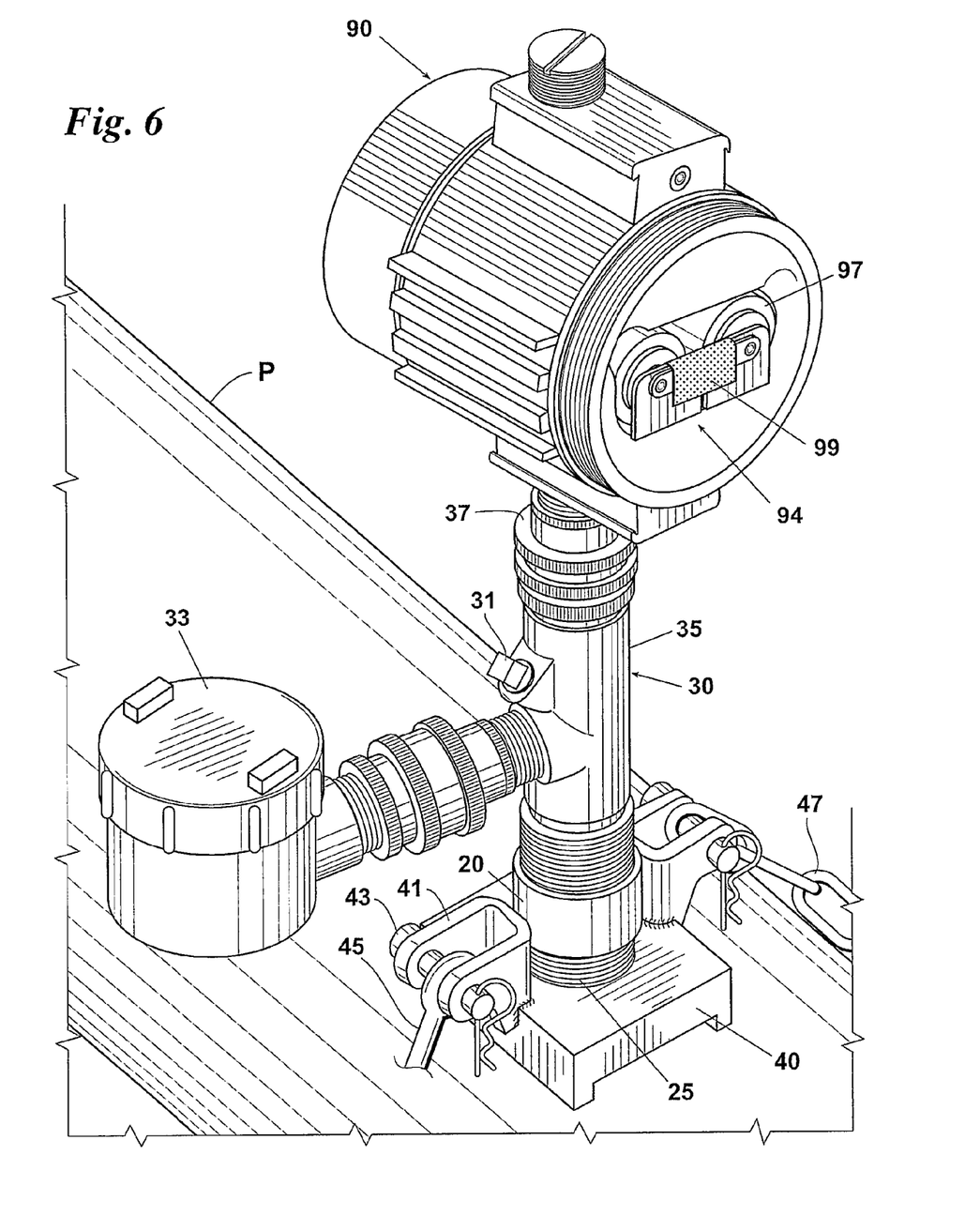
FIG. 6 is a rear isometric view of the detector illustrated in FIG. 1 with the rear cap removed from the display housing. Because the batteries engage spring-loaded contacts within the display unit, all electrical contact with the batteries is broken prior to the rear cap being completely removed. A sheet of insulating padding, preferably affixed to the underside of the rear cap, resides between the batteries and the cap to prevent electrical contact with the cap.
Figure 7:
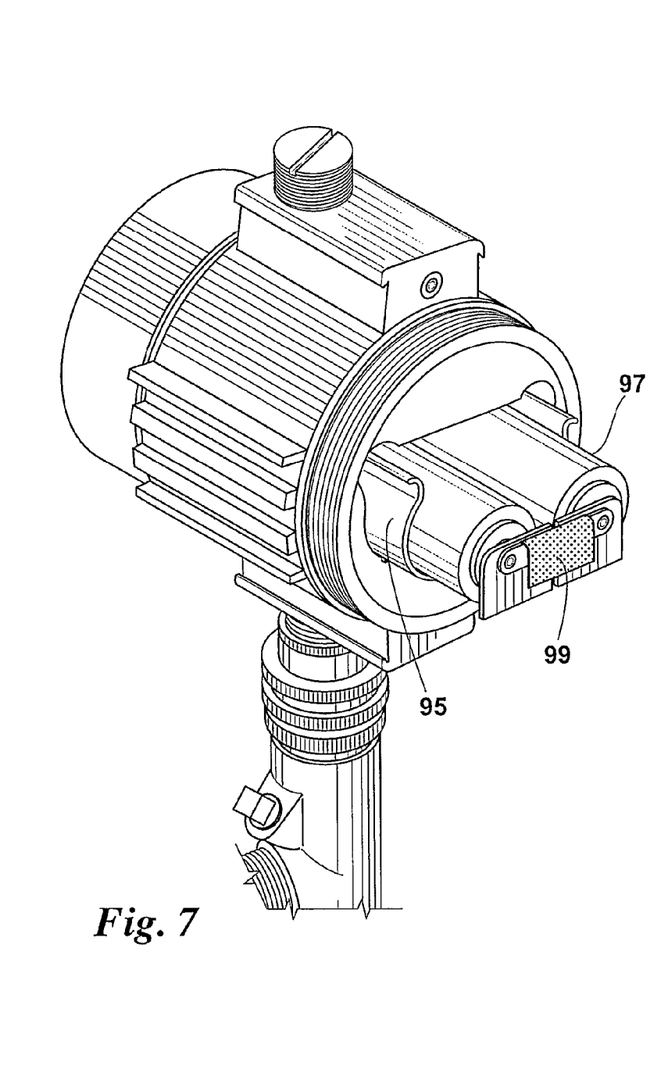
FIG. 7 is a partial, rear isometric view of the display housing illustrated in FIG. 1. The batteries reside in a cradle/battery holder that is received by the insert body.

As illustrated in FIGS. 6 & 7, display unit 70 preferably includes a battery pack 94. The cradle/battery holder 95 in which the batteries 97 resides is received by an interior space of the display insert 70. Spring-loaded contacts (not shown) within display insert 70 urge against the distal end of battery pack 94 so that as a user unthreads the rear cap 93 of display housing 90, battery pack 94 is urged away from the contacts and toward the retreating rear cap 93. The connection between the spring-loaded contacts and battery pack 94 is, therefore, broken prior to rear cap 93 being completely removed from housing 90. This feature provides for use of detector 10 in explosion-proof zones. An insulating pad 99 is provided between the proximal end of battery pack 94 and rear cap 93.

Referring now to FIGS. 8 to 11B, sensor housing 20 houses a sensor board 50. A microcontroller 51 on the sensor board 50 receives data collected by magnetometer sensor 60 and runs detection algorithm 100 (see FIG. 12) to determine whether a passage event has occurred. Microcontroller 51, which is of a type well known in the art, is in communication with the display unit 70 or other systems by way of a communication interface 55. In a preferred embodiment, interface 55 is a RS485 interface. Board 50 also includes an oscillator 53 made up of a comparator, an analog switch array and an AND gate array.

Figure 11A:
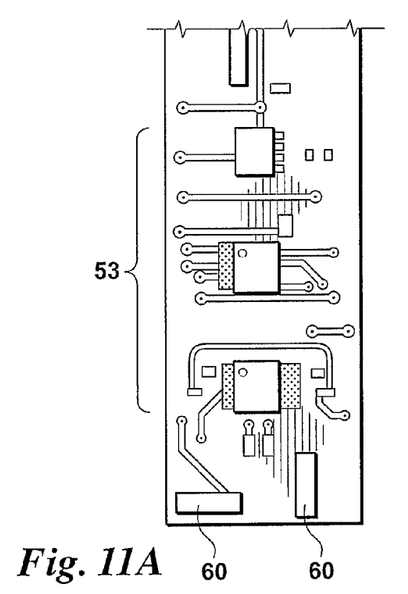
FIGS. 11A & 11B illustrate alternate embodiments of the sensor board of FIG. 8. Two sensors are arranged orthogonal to one another. The sensor board may use a 1-D, 2-D, 3-D or n-D array of sensors which may differ in orientation and separation of the sensor elements. Orthogonal orientations, however, are preferred.
Figure 11B:
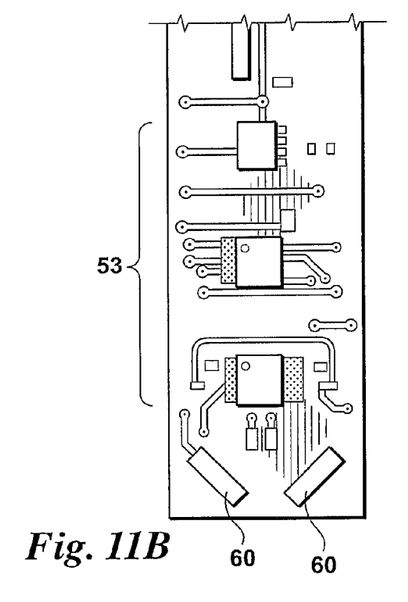

Detector 10 may use a 1-D, 2-D, 3-D, or n-D array of magnetometer sensors 60 which may differ in orientation relative to one another, separation of the individual sensor elements, or both. Orthogonal orientations, as illustrated in FIGS. 11A & B, are preferred when multiple sensors 60 are used. Sensors 60 with a common orientation but that are offset may be used to improve the detection process using coincidence (or correlation) algorithms.

Various magnetometer technologies may be employed for sensor 60. In a preferred embodiment, sensor 60 is a magnetic flux sensor using a variable permeability material. Changes in the flux alter the effective inductance of the magnetometer. A flux sensor manufactured by PNI Corporation, Inc. (Santa Rosa, Calif.) is an effective magnetic flux sensor 60.

Digital signal processing is essential to the detection process and a digital, adaptive detection algorithm is the preferred signal processing algorithm. As illustrated in FIG. 12, the detection scheme is an adaptive thresholding detection process 100 based on a real-time noise estimate for the sensor (s) 60. Parameterization allows process 100 to be adjusted for the widest application with a minimum of false alarms and a high probability of detection. Preferred range and values for critical parameters are indicated in the description of process 100 below.

Detection process 100, which is implemented by microcontroller 51, may include all of the following processing steps: automatic elimination of outliers, computation and removal of the measurement offset, estimation of the measurement noise, establishing threshold(s) with and without hysteresis, sequential detection, and event time discrimination/detection. Sensor(s) 60 collect magnetometer data 101 ("mag data" or mag) for processing and detection event 103 is determined by a number of criteria including but not limited to amplitude, duration, and previous events. The fine structure of the response of sensor(s) 60 may also be accounted for by using pattern recognition techniques.

Mag data 101 is first processed by processing step 110, elimination of outliers:

$$\text{mag}_i = \min(\text{mag}_i - \text{baseline estimate}_{i-1} * \text{signum}(\text{mag}_i), \text{outlier limit}) \quad \text{(Eq. 1)}$$

See FIG. 13 & sub-steps 113-117. After removal of the offset (baseline) from the measurement, the input is limited to less than or equal to the outlier limit. The sign is preserved over the operation. The "signum" function returns the sign of the argument. The "min" function returns the arithmetical minimum of the argument list. The outlier-free magnetometer data are then returned to process 100 and passed through a low pass filter to estimate the baseline.

Figure 14:
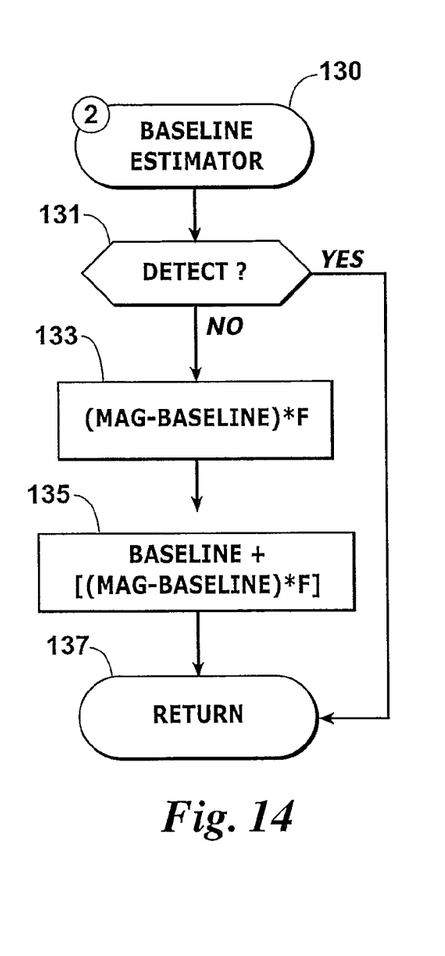
FIG. 14 is a flowchart of the baseline estimation step of the algorithm illustrated in FIG. 12.

Processing step 130, estimation of the baseline, is:

$$\text{baseline estimate}_i = \text{baseline estimate}_{i-1} + (\text{mag}_i - \text{baseline estimate}_{i-1}) * f/65536 \quad \text{(Eq. 2)}$$

See FIG. 14 & sub-steps 131-137. Processing step 130 is a low pass filter which is used to estimate the offset from zero for the measurement. The low pass filter is a simple exponential type. The transfer function for the filter is:

$$H_1(z) = \frac{b_0 + b_1 z^{-1} + b_2 z^{-2}}{a_0 + a_1 z^{-1} + a_2 z^{-2}} \quad \text{(Eq. 3)}$$

where:

$$b = \left[ \frac{f}{65536} \quad 0 \quad 0 \right]$$

$$a = \left[ 1 \quad \left( \frac{f}{65536} - 1 \right) \quad 0 \right]$$

The value for time constant "f" may be in the range of 1 to 4096. The preferred value for "f" is 128. The baseline estimate is:

$$\text{baseline estimate} = H_{1(z)} * \text{mag} \quad \text{(Eq. 4)}$$

Figure 15:
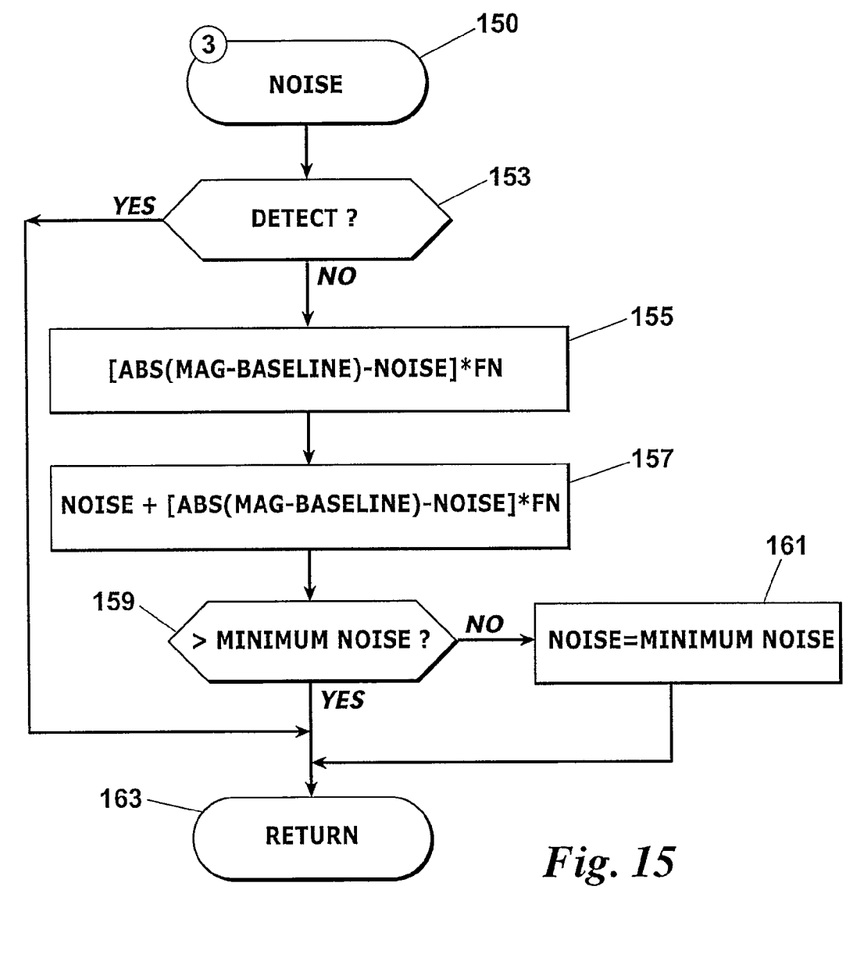
FIG. 15 is a flowchart of the noise estimation step of the algorithm illustrated in FIG. 12.

Processing step 150 provides a noise estimate:

$$\text{noise}_i = \quad \text{(Eq. 5)}$$

$$\max\left( \text{noise}_{i-1} + \left( \text{abs}((\text{mag}_i - \text{baseline estimate}_{i-1}) - \text{noise}_{i-1}) * \frac{fn}{65536}, \min \text{noise} \right) \right)$$

See FIG. 15, sub-steps 151-163. This is a low pass filter which produces a noise estimate for the adaptive threshold selection required by the detection process. The noise level is always positive and is bounded by a minimum. The transfer function for the filter is:

$$H_2(z) = \frac{b_0 + b_1 z^{-1} + b_2 z^{-2}}{a_0 + a_1 z^{-1} + a_2 z^{-2}} \quad \text{(Eq. 6)}$$

where:

$$b = \left[ \frac{fn}{65536} \quad 0 \quad 0 \right]$$

$$a = \left[ 1 \quad \left( \frac{fn}{65536} - 1 \right) \quad 0 \right]$$

The value for time constant "fn" may be in the range of 1 to 256. The preferred value for "fn" is 32. The noise estimate is:

$$\text{noise} = H_{2(z)} * (\text{abs}(\text{mag} - \text{baseline})) \quad \text{(Eq. 7)}$$

Figure 16:
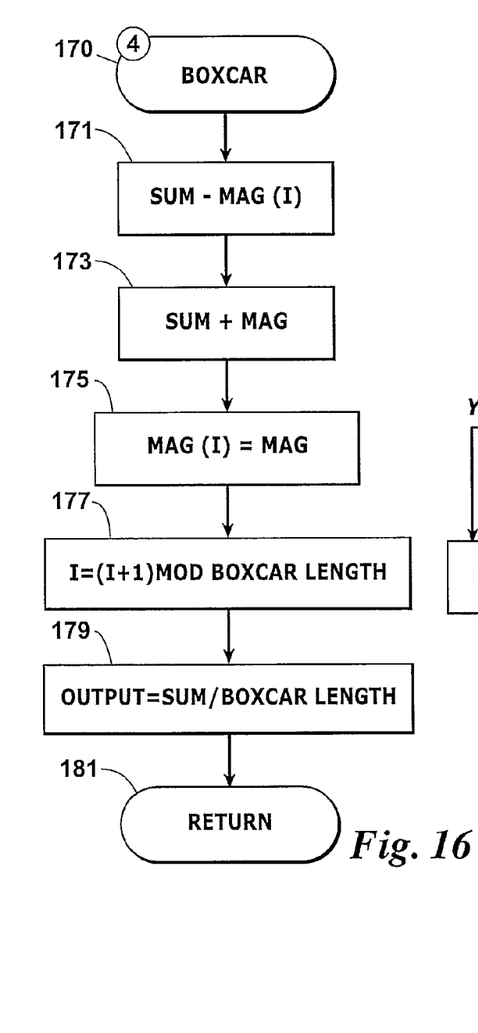
FIG. 16 is a flowchart of the boxcar or input smoothing step of the algorithm illustrated in FIG. 12.

The input magnetometer values are then smoothed using a "boxcar" low pass filter in processing step 170. See FIG. 16, sub-steps 171-181. The structure of the filter is:

$$H_{3(z)} = \frac{1}{n} \sum_{i=0}^{n-1} (\text{rectangular window}[i] * z^{-i}) \quad \text{(Eq. 8)}$$

This filter is used to shape the response after magnitude processing (absolute value). The length of the rectangular window may be in the range of 2 to 128. In the preferred configuration the length is 32.

Figure 17:
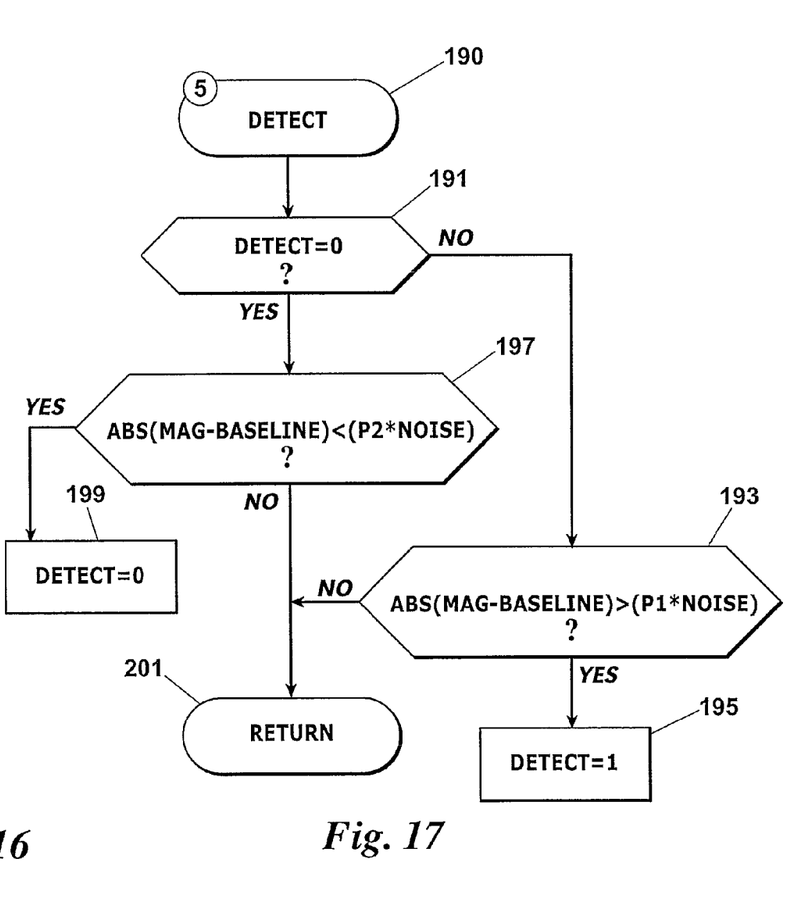
FIG. 17 is a flowchart of the detector step of the algorithm illustrated in FIG. 12.

Following input smoothing, the detection process occurs in processing step 190. See FIG. 17, sub-steps 191-201. The detection process is a sequential process which includes the previous value of the detector. If the current value of the detector is "off" and the smoothed magnitude is greater than the upper threshold, the detector is switched "on." If the detector is "on" and the smoothed magnitude is less than the lower threshold, the detector is switched "off." Other conditions for the input result in no change in the detector value. In equation form:

if $(H_{3(z)} * (\text{abs}(\text{mag}_i) - \text{baseline estimate}_i) \geq \text{upper threshold}_i)$ and $(\text{detector}_{i-1} = 0)$ then $\text{detector}_i = 1$ (Eq. 9a)

If $(H_{3(z)} * (\text{abs}(\text{mag}_i) - \text{baseline estimate}_i) \leq \text{lower threshold}_i)$ and $(\text{detector}_{i-1} = 1)$ then $\text{detector}_i = 0$ (Eq. 9b)

else $\text{detector}_i = \text{detector}_{i-1}$ (Eq. 9c)

The determination of the upper and lower detection thresholds is:

$$\text{upper threshold}_i = p1 * \text{noise}_i \quad \text{(Eq. 10a)}$$

$$\text{lower threshold}_i = p2 * \text{noise}_i \quad \text{(Eq. 10b)}$$

The value for p1 and p2 may be in the range of 1 to 10. The preferred value for p1 is 3. The preferred value for p2 is 1.

Figure 18:
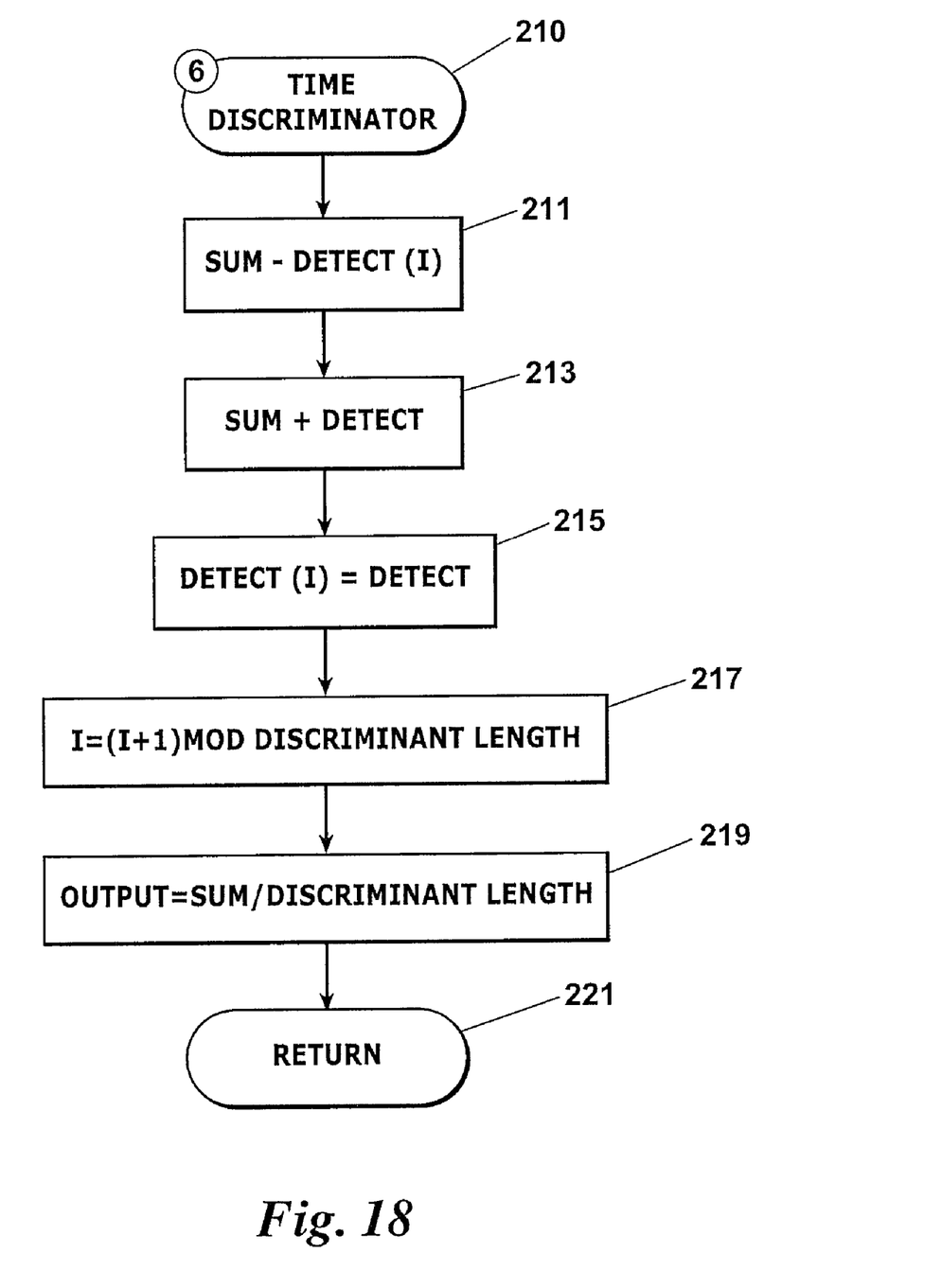
FIG. 18 is a flowchart of the time discriminator step of the algorithm illustrated in FIG. 12.

Following a detection event, processing step 210 uses time to determine the extent of the event. See FIG. 18, sub-steps 211 to 221. One or more filters of the following type may be used to characterize the event to determine if single or multiple events are present:

$$H_{4(z)} = \frac{1}{m} \sum_{i=0}^{n-1} \text{rectangular window}[i] * z^{-i} \quad \text{(Eq. 11)}$$

where $$m \leq n$$

This transfer function operates on the detected output, whose value is 0 or 1. Various lengths of rectangular windows can be used to discriminate between short and long events. The longest window, passing the detection limit, indicates the extent of a single event:

$$\text{event detect} = H_{4(z)} * \text{detect} \quad \text{(Eq. 12)}.$$

Figure 19:
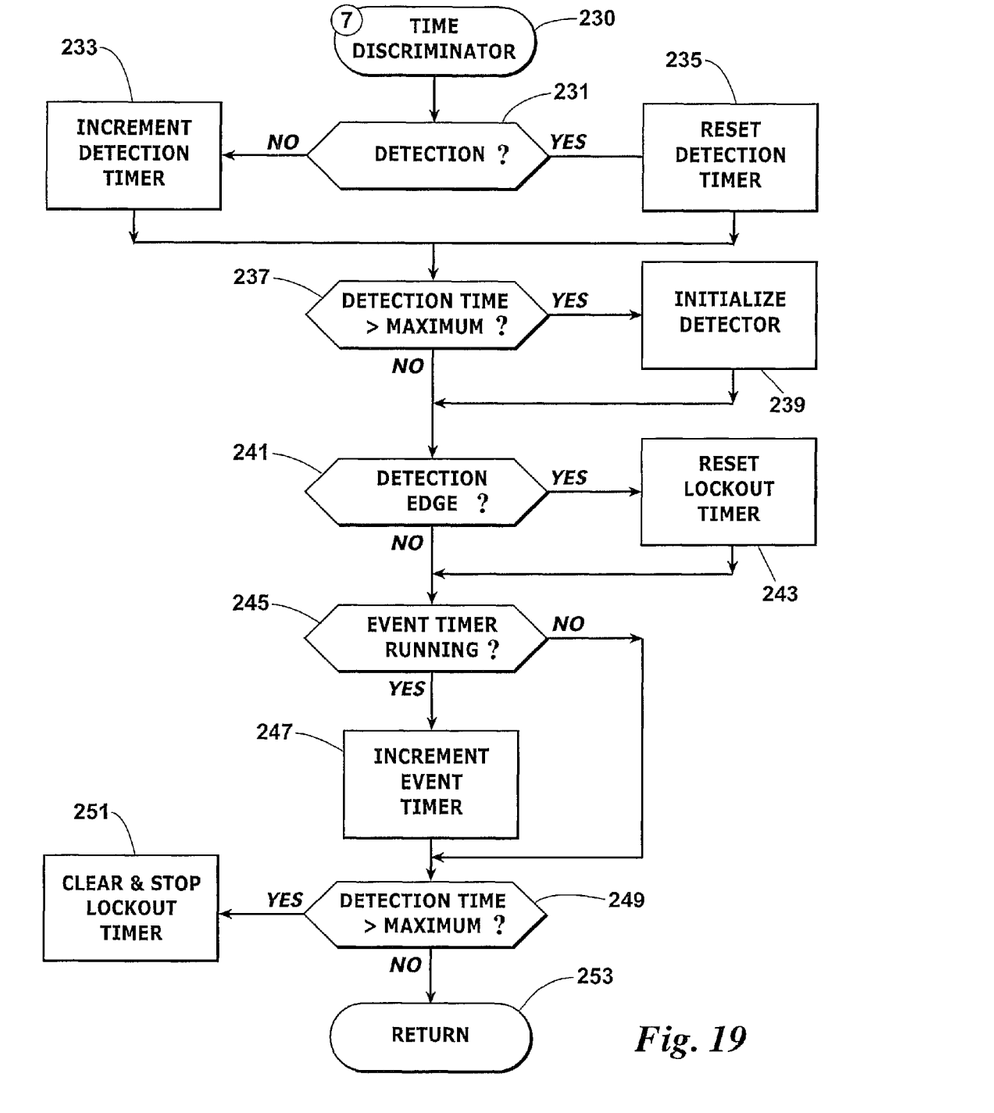
FIG. 19 is a flowchart of the Bayesian lockout step of the algorithm illustrated in FIG. 12.

Because a single pig or object may present multiple magnetic fields, processing step 230, lockout discriminator, may be employed to prevent multiple passage events being detected for a single object as the object passes by detector 10. See FIG. 19, sub-steps 231 to 253. In a preferred embodiment, processing step 230 employs a Bayesian lockout estimator. If there is a passage event, then a detection timer is incremented and further detection is locked-out for a predetermined time period. Once the predetermined time period is exceeded, the detector is unlocked and initialized and the lockout timer is stopped and cleared until the next detection event. Similar to reed switch 89B, processing step 230 provides the ability to control unwanted detection.

While detector 10 and process 100 have been described with a certain degree of particularity, many changes may be made in the details of construction and the arrangement of components or steps without departing from the spirit and scope of this disclosure. The invention, therefore, is not limited to the embodiments set forth herein for purposes of exemplification, but is to be limited only by the scope of the attached claims, including the full range of equivalency to which each element thereof is entitled.

What is claimed is:

1. A system for detecting the passage of an object in a pipeline, the system comprising:
    a detector configured for arrangement about and secured to an external surface of the pipeline and including at least one magnetometer sensor;
    a shielding surrounding the at least one magnetometer sensor; and
    a microcontroller in communication with the at least one magnetometer sensor and having an adaptive thresholding detection means for processing a magnetic flux data stream collected by the at least one magnetometer sensor and detecting a passage event;
    the adaptive thresholding detection means calculating a baseline estimate and a noise estimate and using the baseline and noise estimates to determine an upper threshold and a lower threshold, the upper threshold being used to detect movement and the lower threshold being used to reset the detector.

2. A system according to claim 1 further comprising a second magnetometer sensor housed by the detector and being offset relative to said at least one magnetometer sensor.

3. A system according to claim 1 further comprising a display module in communication with said microcontroller.

4. A system according to claim 1 further comprising said adaptive thresholding detection means including a low pass filter.

5. A system according to claim 1 further comprising means for preventing detection by the detector of a passage of an object in a pipeline.

6. A system according to claim 5 wherein said preventing means is a reed switch.

7. A system according to claim 5 wherein said preventing means is a Bayesian lockout estimator.

8. A system according to claim 1 further comprising means for adjusting a position of the detector relative to the external surface of the pipeline.

9. A system according to claim 1 further comprising a detachably secured base receiving a portion of said detector.

10. A system according to claim 1 further comprising said shielding being a magnetic permeable shielding.

11. A system according to claim 1 further comprising said shielding being an electrical insulating shielding.

12. A system according to claim 1 further comprising a backup power source, said backup power source configured to break electrical contact prior to exposure to ambient environment.

13. A method for detecting the passage of an object in a pipeline, the method comprising the steps of:
    securing a detector housing at least one magnetometer sensor on an exterior surface of the pipeline;
    collecting a magnetic fax data stream from the at least one magnetometer sensor;
    processing the magnetic flux data stream through an adaptive thresholding detection algorithm; and
    using the processed magnetic flux data stream to detect a passage event;
    wherein the adaptive thresholding detection algorithm calculates a baseline estimate and a noise estimate and uses the baseline and noise estimates to determine an upper threshold and a lower threshold, the upper threshold being used to detect movement and the lower threshold being used to reset the detector.

14. A method according to claim 13, said processing step further comprising the step of passing the magnetic flux data through at least one low pass filter.

15. A method according to claim 13, said processing step further comprising the step of removing outlier data from the magnetic flux data stream to provide an outlier-free magnetic flux data stream.

16. A method according to claim 15, said removing step including the steps of:
    removing a baseline value from the magnetic flux data stream; and
    limiting the magnetic flux data stream to a value no greater than an outlier limit.

17. A method according to claim 15 further comprising the step of passing the outlier-free magnetic flux data stream through a first low pass filter to estimate a baseline.

18. A method according to claim 15 further comprising the step of passing the outlier-free magnetic flux data stream through a low pass filter to produce a noise estimate.

19. A method according to claim 15 further comprising the step of passing the outlier-free magnetic flux data stream through a low pass filter to produce a smoothed magnitude of the outlier-free magnetic flux data stream.

20. A method according to claim 15 further comprising the step of comparing a smoothed magnitude of the outlier-free magnetic flux data stream to a set of detection limits.

21. A method according to claim 20 further comprising the step of passing the smoothed magnitude through a low pass filter to determine a length of a detection event.

22. A method according to claim 13 further comprising the step of counting a detection event.

23. A method according to claim 13 further comprising the step of displaying the detection event.

24. A method according to claim 13 further comprising signaling a remote device based upon the passage event.

25. A method according to claim 13, further comprising the step of preventing detection of a non-passage event.

26. A method according to claim 25 further comprising said preventing step including the sub-step of locking out the detector.

27. A method according to claim 25 further comprising said preventing step including the sub-step of locking out the detector for a predetermined time period after the passage event.

28. A method according to claim 13, said processing step further comprising the sub-step of estimating a noise estimate.

29. A method according to claim 13, said processing step further comprising the sub-step of smoothing a magnitude of the magnetic flux data stream.

30. A method according to claim 13, said processing step further comprising the sub-steps of:
    determining an upper and a lower detection threshold value;
    comparing a smoothed magnitude of the magnetic flux data stream to at least one of the upper and lower detection thresholds; and updating a detector value based upon a result of the comparison.

31. A method according to claim 13 further comprising said processing step including the sub-step of determining a time length of the detection event.

32. A pipeline pig system comprising:
a detector configured for arrangement about an external surface of the pipeline and including a housing having at least one magnetometer sensor;
a shielding surrounding the at least one magnetometer sensor;
microcontroller in communication with the at least one magnetometer sensor and having an adaptive thresholding detection means and a first, a second, a third, and a fourth low pass filter;
the adaptive thresholding detection means removing outlier data from a magnetic flux data stream to provide an outlier-free magnetic flux data stream;
the first low pass filter processing the outlier-free magnetic flux data stream to estimate a baseline;
the second low pass filter processing the outlier-free magnetic flux data stream to produce a noise estimate;
the third low pass filter processing the outlier-free magnetic flux data stream to produce a smoothed magnitude of the outlier-free magnetic flux data stream;
the fourth low pass filter processing the smoothed magnitude of the outlier-free magnetic flux data stream to determine the length of a detection event.

* * * * *